(12) United States Patent
Wiebe et al.

(10) Patent No.: US 12,714,858 B2
(45) Date of Patent: Aug. 25, 2026

(54) MEDICAL DEVICE FOR CLOSED LOOP VAGAL NERVE STIMULATION

(71) Applicant: ADRAXE CORPORATION, Plymouth, MN (US)

(72) Inventors: Sherman P. Wiebe, Brussels (BE); Andrew N. Csavoy, Dallas, TX (US)

(73) Assignee: Adraxe Corporation, Plymouth, MN (US)

( * ) Notice: Subject to any disclaimer, the term of this patent is extended or adjusted under 35 U.S.C. 154(b) by 305 days.

(21) Appl. No.: 18/345,693

(22) Filed: Jun. 30, 2023

(65) Prior Publication Data

US 2024/0009456 A1 Jan. 11, 2024

Related U.S. Application Data

(60) Provisional application No. 63/359,332, filed on Jul. 8, 2022.

(51) Int. Cl.

| | |
|---|---|
| ***A61N 1/36*** | (2006.01) |
| ***A61N 1/02*** | (2006.01) |
| ***A61N 1/372*** | (2006.01) |
| *A61N 1/05* | (2006.01) |

(52) U.S. Cl.

CPC ......... *A61N 1/36053* (2013.01); *A61N 1/025* (2013.01); *A61N 1/3614* (2017.08); *A61N 1/36146* (2013.01); *A61N 1/37211* (2013.01); *A61N 1/0529* (2013.01); *A61N 1/36064* (2013.01)

(58) Field of Classification Search

CPC .. A61N 1/025; A61N 1/0529; A61N 1/36053; A61N 1/36064; A61N 1/3614; A61N 1/36146; A61N 1/37211

See application file for complete search history.

(56) References Cited

U.S. PATENT DOCUMENTS

2014/0288620 A1* 9/2014 DiLorenzo ......... A61N 1/36053 607/62

* cited by examiner

*Primary Examiner* — Amanda K Hulbert

(74) *Attorney, Agent, or Firm* — Fredrikson & Byron, P.A.

(57) ABSTRACT

This disclosure relates to medical implant systems and apparatuses capable of treating a seizure condition through the use of recording and stimulating electrodes. The apparatus includes an internal pulse generator in communication with a wireless communication module; one or more recording electrodes in communication with the internal pulse generator, wherein the one or more recording electrodes are configured to monitor to detect one or more field potentials produced by neural tissue in proximity to the one or more recording electrodes; one or more stimulating electrodes in communication with the internal pulse generator, wherein the one or more stimulating electrodes are configured to stimulate the vagus nerve.

11 Claims, 6 Drawing Sheets

MEDICAL DEVICE FOR CLOSED LOOP VAGAL NERVE STIMULATION

RELATED APPLICATION

This application claims the benefit of U.S. Provisional App. No. 63/359,332, filed on 8 Jul. 2022, the disclosure of which is incorporated, in its entirety, by this reference.

TECHNICAL FIELD

The present disclosure relates to medical implant devices, such as implanted medical devices that can be used to record and stimulate neurological tissue.

BACKGROUND

In recent years, advances in the field of neuroscience and medicine have better enabled scientists and clinicians to record and modulate neurological activity in humans. The advances were driven, in part, due to a better understanding of the scope and impact that potentially treatable neurological disorders have on individuals and society at large. As one particular example, it is suspected that approximately 3 million or more people in the United States alone suffer from epilepsy, a seizure inducing a debilitating neurological condition.

Fortunately, these neuroscientific advances have allowed scientists and researchers to better observe the real time function of human nervous system, and to also modulate the human nervous system for therapeutic effect (modulation may be achieved through the application of electrical, mechanical, magnetic, photonic, or electromagnetic stimulation). In the case of epilepsy or depression, vagus nerve stimulation, or "VNS," is a neuromodulation technique that may provide therapeutic effects in patients.

The vagus nerve, which is the stimulation target of VNS, is an important cranial nerve thought to be involved in the regulation of organ function, and other bodily functions. The vagus nerve is known to be included in many direct and indirect neurological signal pathways to various central nervous system locations, including the solitary tract, the locus coeruleus and the nucleus basalis. Further, the vagus nerve is also thought to be included in direct and indirect neurological signal pathways to diverse cortical and subcortical brain regions.

By stimulating the vagus nerve through a VNS protocol, it is possible to modulate a diverse range of neurological tissue. VNS is believed to produce this modulation by inducing the vagus nerve to send afferent neurological signals to various central nervous system regions, including the brainstem, hippocampus, thalamus, and cerebral cortex. It is believed that these afferent neurological signals from the vagus nerve suppress cortical tissue excitability, thereby inducing the recipient cortical tissue to create new electrical connections.

Because of this suppression of tissue excitability, and creation of new neurological connections, vagus nerve stimulation therapies may have applications for the treatment of epileptic disorders. One example of such a vagus nerve stimulation therapy is described in U.S. Pat. No. 10,406,363 ("Sabesan"). Sabesan discloses a device for VNS therapy that relies on the evaluation of EEG synchronization, in relation to the delivery of a VNS therapy.

In addition, Sabesan discloses a number of studies conducted relating to EEG and the delivery of VNS therapy. Sabesan discussed one study conducted by Hammond et al., titled "Electrophysiological studies of cervical vagus nerve stimulation in humans: I. EEG effects" as proof that VNS may interrupt ongoing ictal EEG activity.

Sabesan further cites Koo et al. as revealing a progressive decrease in duration and frequency of spikes and wave activity on interracial EEG signals by long-term monitoring of the effects of chronic VNS in "EEG changes with vagus nerve stimulation." Sabesan additionally cites Kuba et al. as showing that acute stimulation of vagal nerves reduces the number of interictal epileptiform discharges where the reduction is most prominent during the stimulation periods in "Effect of vagal nerve stimulation on interictal epileptiform discharges: a scalp EEG study."

Sabesan further cites Marrosu et al. as using a EEG frequency profile in a study to determine the effect of chronic VNS therapy, as described in "Increase in 20-50 Hz (gamma frequencies) power spectrum and synchronization after chronic vagal nerve stimulation." Further, Sabesan also cites Marrosu et al. as an evaluation of the power spectrum density and synchronization from EEGs before and after VNS therapy and identified decreases in the synchronization in theta band and increases in power spectrum and synchronization in gamma (20-50 Hz) after VNS therapy.

Additionally, Sabesan cites Fraschini et al., titled "VNS induced desynchronization in gamma bands correlates with positive clinical outcome in temporal lobe pharmacoresistant epilepsy," as using a phase lag index to compare the EEG synchronization in responders and non-responders to chronic VNS therapy. Sabesan describes that Fraschini et al. found a statistical decrease in de-synchronization in gamma band after five years from VNS surgery, in responders to the VNS therapy, while the other frequency bands do not show significant variation.

Last, Sabesan cites Vos et al. as using a pairwise derived brain symmetry index (pdBSI) to indicate a possibility of predicting a response to VNS therapy from interictal EEG before the onset of VNS therapy, as described in "Predicting success of vagus nerve stimulation (VNS) from interictal EEG." Sabesan states that Vos et al. realized, on average, lower pdBSI values in responders than non-responders in all four frequency sub-bands of $\delta$, $\theta$, $\alpha$, and $\beta$, where the average pdBSI is significantly discriminating between responders and non-responders in the two frequency sub-bands of $\theta$ and $\alpha$. Sabesan states that Vos et al. concluded that pdBSI could be used as a feature to predict the response to VNS therapy as the responders have, on average, less asymmetric spectral characteristics of the interictal EEG than non-responders.

However, Sabesan's device, and the current state of the art for VNS therapy is limited at least in its application due to dependence on EEG synchronization. Because of this shortcoming (and others), improvement in the state of the art is still greatly needed, and in particular with respect to VNS, for the treatment of neurological conditions.

The subject matter claimed herein is not limited to embodiments that solve any disadvantages or that operate only in environments such as those described above. Rather, this background is only provided to illustrate one example technology area where some embodiments described herein may be practiced.

SUMMARY

This disclosure relates to medical implant systems and apparatuses. One embodiment includes an apparatus capable of treating a seizure condition through the use of recording and stimulating electrodes. The apparatus includes an internal pulse generator in communication with a wireless communication module; one or more recording electrodes in communication with the internal pulse generator, wherein the one or more recording electrodes are configured to monitor to detect one or more field potentials produced by neural tissue in proximity to the one or more recording electrodes; one or more stimulating electrodes in communication with the internal pulse generator, wherein the one or more stimulating electrodes are configured to stimulate the vagus nerve.

Another embodiment includes an apparatus capable of treating a seizure condition through the use of recording and stimulating electrodes. The apparatus includes a first internal pulse generator; a second internal pulse generator; a wireless communication module in communication with the first internal pulse generator and the second internal pulse generator; one or more recording electrodes in communication with the first internal pulse generator, wherein the one or more recording electrodes are configured to monitor for one or more field potentials produced by neural tissue in proximity to the one or more recording electrodes; one or more stimulating electrodes in communication with the second internal pulse generator, wherein the one or more stimulating electrodes are configured to stimulate the vagus nerve.

Yet another embodiment of the present disclosure relates to a method treating a seizure condition through the monitoring and characterization of one or more electrical signals produced by neural tissue. The method includes delivering a first vagus nerve stimulation therapy with one or more stimulating electrodes; detecting a first set of one or more field potentials from the neural tissue in proximity to one or more recording electrodes; analyzing the first set of one or more field potentials to determine a first set of one or more brain states; modulating a VNS protocol based on the first set of one or more brain states; delivering a modulated vagus nerve stimulation protocol with one or more stimulating electrodes; and repeating the method steps.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1:
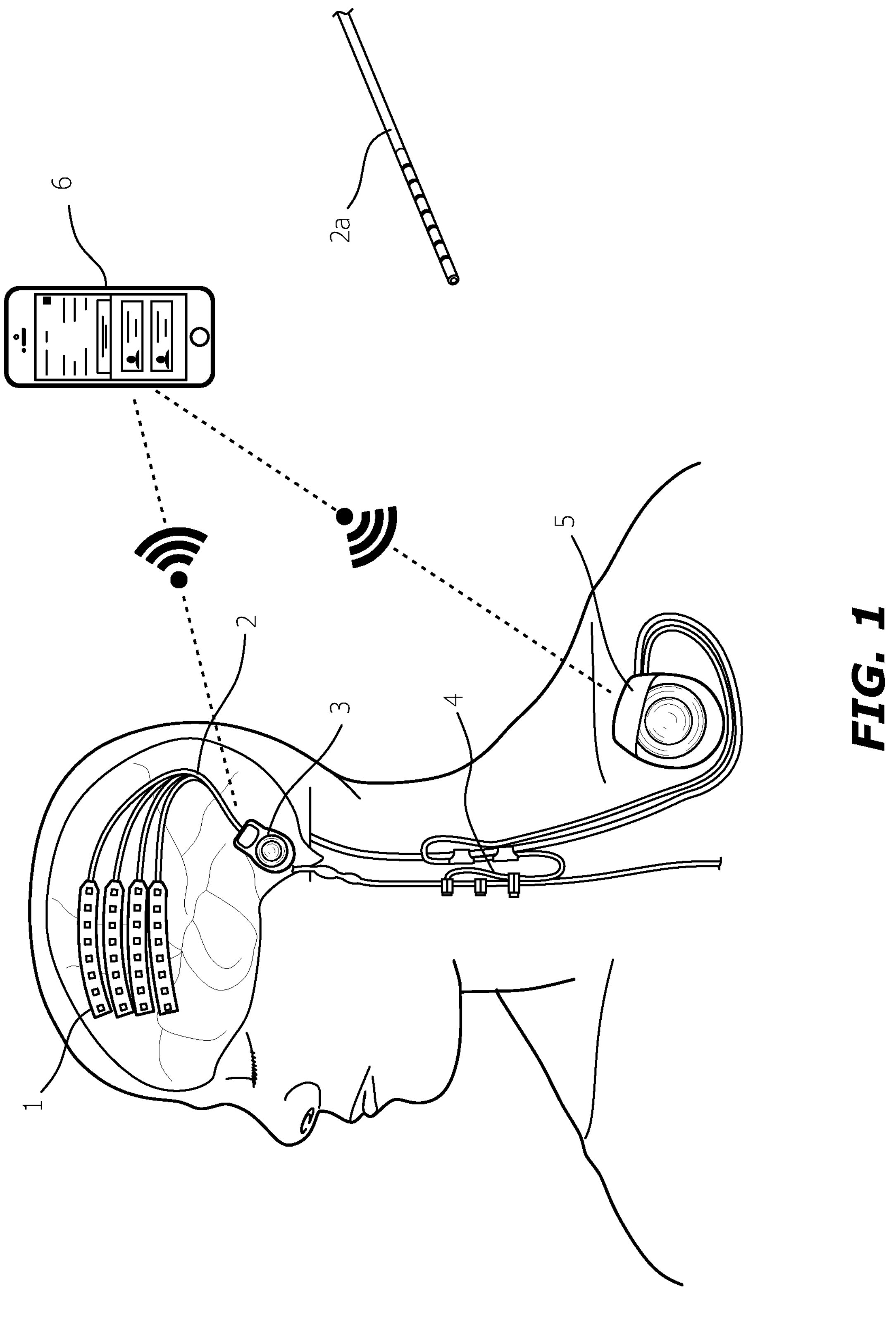
FIG. 1 is a diagram of one embodiment of a medical implant system that can be used for vagus nerve stimulation therapy.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

In recent years, advances in medical science have made it possible to modulate and sense the activity of the neural systems in both humans and animals. These advances have allowed scientists and researchers to interact with and observe the various neural systems in more detail than had previously been possible. Some approaches to interacting with and observing various neural systems include the use of processing machines configured to observe or record neural activity, and in some cases even stimulate neural activity. The various approaches have varying scope and accompanying limitations in terms of degree of access, specificity, precision, and/or accuracy of recording signals and/or delivering signals that stimulate neural activity.

According to an exemplary embodiment, the apparatuses, systems, and methods of the present disclosure herein are used to determine the efficacy of applying VNS therapy to patients that have depression or epileptic events. In some embodiments, a medical implant system may be configured to record field potentials of the brain. A field potential may be described as a transient electrical signal generated by the nervous system through the summed and synchronous electrical activity of the individual cells in a given portion of neural tissue. EEG is a method to record the macroscopic electrical activity of the brain, such as field potentials. In some embodiments, a medical implant system may record field potentials of the brain using one or more recording electrodes. The one or more recording electrodes may be implanted under the skin in the subgaleal space, or may be placed above the skin through the use of an EEG cap, and may record neurological signals via EEG.

In some embodiments, the medical implant system may determine whether the recorded field potentials exhibit characteristics indicative of depression, or an imminent or actively occurring epileptic event. In some embodiments, the recorded field potentials may be characterized, and this characterization may include an analysis of the phase amplitude cross frequency coupling, cross frequency coherence, frequency coupling and coherence across one or more electrode channels, and or phase coupling and coherence across one or more electrode channels.

In some embodiments, the recorded field potentials may be analyzed and characterized using spectral analysis. For example, a Hilbert transform may be used to analyze the instantaneous and near-instantaneous power in recorded EEG signals at different frequency bands. These frequency bands may include delta (<4 Hz), theta (4-8 Hz), alpha (8-12 Hz), beta (12-30 Hz), gamma (30-80 Hz), high-gamma (>80 Hz). If necessary, these recorded EEG signals may be normalized using known techniques. These recorded signals may be analyzed to determine the relative mean power as a percentage decrease or increase of mean power relative to a baseline, the ratios of mean power between any two spectral power bands (e.g. gamma band power divided by alpha band power, gamma band power divided by theta band power, etc.), and the differential power ratios in certain frequency bands across the one or more recording electrodes (e.g., the difference between the gamma band power between the one or more recording electrodes, etc.). This analysis may provide indicators of specific brain states, which can be used to determine whether a VNS protocol should be administered, and to control the VNS stimulation protocol to either increase or decrease the amplitude, frequency, pulse width, duty cycle, mode (e.g. tonic high frequency, theta-burst), or duration of the VNS stimulation.

In another example, the recorded field potentials may be analyzed and characterized based on recorded vagal evoked potentials. Vagal evoked potentials are compound waveforms produced through VNS that comprise several phases. The early phase of a vagal evoked potential is elicited approximately 5-70 milliseconds post VNS stimulation, the immediate phase is elicited approximately 70-250 milliseconds post VNS stimulation, and the late phase is elicited 250-700 milliseconds post VNS stimulation. These vagal evoked potentials may be modulated by the brain state of the patient and their ongoing cortico-thalamic activity at the time the VNS stimulation is delivered. Each of these vagal evoked potential phases may have aspects that can be analyzed. These may include peak amplitude, peak-to-trough amplitude, root-mean-square power, and ratios of any combination of these measures across the one or more recording electrodes.

The analysis of these field potential characteristics may be used separately or in conjunction with one another to determine a modulation protocol for VNS. In some embodiments, the medical implant system may deliver VNS therapy to the vagus nerve of a patient. By stimulating the vagus nerve with a burst stimulation protocol, VNS therapy may produce vagal evoked potentials in diverse areas of the nervous system. The medical implant system may record field potentials produced by the neural tissue in proximity to the recording electrodes, which may include field potentials generated by the VNS. The characterization of the recorded field potentials may indicate one or more brain states of a patient receiving VNS. These one or more brain states may be used to determine and deliver a modulated VNS protocol.

For example, the characterization of field potentials in proximity to the one or more recording electrodes may indicate one or more brain states of a patient where modulation of a VNS protocol should be performed. In one example, the one or more brain states may indicate whether additional VNS protocol should be administered, or whether modulated VNS stimulation protocol should be applied to either increase or decrease the amplitude, frequency, pulse width, duty cycle, mode (e.g. tonic high frequency, theta-burst), or duration of the VNS stimulation. The present embodiment thereby enables "closed-loop" feedback for VNS therapy that is configured to iteratively determine one or more brain states, and dynamically control (and modify) the application of VNS in a tailored fashion responsive to those one or more brain states.

Unlike conventional VNS systems providing standard, cookie-cutter stimulation, the medical implant system of the present disclosure can intelligently provide modulated VNS stimulation protocols that vary in real-time (or near real-time) as the medical implant system determines how different neurological tissues (or brain regions) respond to stimulation. In this manner, the medical implant system can provide variable amounts and types of signaled stimulation over a sequence of stimuli to different neurological tissues. This dynamic approach of the medical implant system can also avoid overstimulation to one neurological tissue and under stimulation to another neurological tissue. Further, using this dynamic approach can lend to increased accuracy and effectiveness of targeted neurological tissue stimulation, whereas some conventional VNS systems blindly stimulate regardless of tissue response.

These and other embodiments are discussed below with reference to FIGS. 1-6. However, those skilled in the art will readily appreciate that the detailed description given herein with respect to these figures is for explanatory purposes only and should not be construed as limiting.

FIG. 1 illustrates one embodiment of a medical implant system that can be used for vagus nerve stimulation therapy. The embodiment includes a first internal pulse generator 3 in communication with a wireless communication module 6; one or more recording electrodes 1 in communication with the first internal pulse generator 3, wherein the one or more recording electrodes 1 are configured to monitor to detect one or more field potentials produced by neural tissue in proximity to the one or more recording electrodes; a second internal pulse generator 5 in communication with a wireless communication module 6; one or more stimulating electrodes 4 in communication with the second internal pulse generator 5, wherein the one or more stimulating electrodes 4 are configured to stimulate the vagus nerve.

The one or more recording electrodes 1 may be implanted in a patient in a subdural location, implanted in the subgaleal space of a patient, and or placed on a patient's scalp using an EEG cap. The one or more recording electrodes 1 can be formed by one or more layers of electrically conducting material and/or electrically insulating material jointly forming electrical access sites. In some embodiments, the one or more recording electrodes 1 can include at least two layers of insulating material and at least one layer of electrically conducting material. In some embodiments, the one or more recording electrodes 1 can be formed with a first electrically insulating layer and a second electrically insulating layer encapsulating an electrically conducting layer sandwiched between the first electrically insulating layer and the second electrically insulating layer. The first insulating layer and/or the second insulating layer can be configured to include openings that permit access to the electrically conducting layer forming the electrical access sites.

In some embodiments, the electrically insulating layers and/or the electrically conducting layer can be formed via deposition of material. For example, in some embodiments, at least one layer of insulating material (e.g., the first electrically insulating layer or the second electrically insulating layer) can serve as a substrate and base layer for all other material layers (e.g., one or more electrically conducting layers, one or more additional electrically insulating layers, etc.) deposited on top of this base layer. In some embodiments, the electrically conducting layer can be patterned to create conducting leads/traces between electrode access sites and a connector interface, as described herein. The electrically conducting layer may be used to electrically couple to and provide access to multiple electrode access sites. In some embodiments, the electrode access sites may include one or more additional electrically conducting layers that may provide additional electrically conducting traces.

In some such embodiments, there may be at least one insulating material layer that encloses each of the electrically conducting layers or electrically conducting traces, electrically insulating the different electrically conductive traces and electrode sites from one another, as well as from the biological environment. In some embodiments, the electrically insulating layer can be patterned to expose (1) the electrode sites at the distal extremity of the electrode array to biological tissue and biological fluids for charge transfer and (2) the bond sites at the proximal extremity of the electrode array serving as interface to the connector.

In some embodiments, the material for forming the electrically insulating layers can be selected based on one or more specific criteria including biocompatible molecular composition, high electrical capacitance, low thermal conductivity and thermal mass, low areal mass density, defect-free, thermal and chemical compatibility with polymer substrates and stability in electrolyte solutions at physiological pH and temperature.

In some embodiments, the electrically insulating layers can be formed from any suitable material including polyimide, silicon carbide, SU-8, a liquid crystal polymer (LCP), Parylene-C, a ceramic, silicon dioxide, silicone, polyurethane, or any combination thereof. The electrically insulating layer can be of any suitable thickness and can be fabricated or formed using any suitable process. For example, in some embodiments, the electrically insulating layer can be formed from an ultrathin layer of thermal silicon oxide which can be transfer bonded.

In some embodiments, the electrically conducting layer can be made from any suitable material including gold, platinum, iridium, iridium oxide, titanium nitride, titanium oxide, MP35N, poly(3,4-ethylenedioxythiophene (PEDOT), graphene, carbon nano-tubes (CNT), PEDOT PSS, or a combination of these materials in form of alloys or material stacks. The electrically conducting layer can be of any suitable thickness and can be fabricated or formed using any suitable process.

The electrically conducting layer can be configured to include electrode access sites that can be arranged in any suitable pattern across the one or more recording electrodes 1. In some embodiments, the electrode access sites can be situated or formed specifically in an area such that there is a desired distance between the two most distant electrode access sites. The desired distance between the two most distant electrode access sites can be any suitable distance based on the application that the device can be used for. For example, the distance can be approximately 1 mm to approximately 50 mm including any measure of distance therebetween. The one or more recording electrodes 1 can be formed to assume any number of geometric shapes that can enable precise recording of electrical activity. In some implementations, the one or more recording electrodes 1 can be chosen to be of a particular shape dependent on the geometric shape of the target tissue and tissue surrounding it. In some implementations, the shape of the one or more recording electrodes 1 can be chosen based on the access to the target tissue for example one or more insertion sites, and/or dependent on the particular recording application desired.

As an example, the electrode access sites may be arranged according to any suitable pattern including a linear pattern, a circular pattern, an array pattern, or any other desired or customized pattern. The electrode access sites may be configured in rows (i.e. 1 row of 8 electrode access sites, 1 row of 4 electrode access sites, 2 rows of 2 electrode access sites, 4 rows of 4 electrode access sites. The number of electrode access sites per the one or more recording electrodes 1 may range between 1 and 64 sites.

The electrode access sites on the one or more recording electrodes 1 may be connected to one or more cables 2. The one or more cables 2 may be subcutaneous implanted. The one or more cables 2 may include a plurality of leads, where each lead may be connected to an electrode access site in a manner that is electrically insulated from other electrode access sites on the one or more recording electrodes 1. Each insulated electrode access site and cable lead pair may be described as a channel. The one or more cables 2 may include one or more terminating pigtail channel connectors 2*a*. The one or more terminating pigtail channel connectors 2*a* may connect one or more channels to the first internal pulse generator 3. The one or more terminating pigtail channel connectors 2*a* may connect a plurality of 8 channels, or 16 channels to the first internal pulse generator 3. For example, four 16 channel pigtail channel connectors 2*a* may connect 64 channels to the first internal pulse generator.

The one or more recording electrodes 1 can be configured to be capable of recording field potentials, EEG signals, and or action potentials. In some embodiments, the recorded local field potentials may be characterized, and this characterization is discussed in more detail in connection with FIG. 2 below.

The first internal pulse generator 3 is described more fully in connection with FIG. 2 below. The first internal pulse generator 3 may be in communication with a wireless communication module 6. The communication may be wireless, wired, and or through various communication protocols such as IR, Bluetooth, UV etc. The first internal pulse generator 3 may communicate to the wireless communication module 6 neural data obtained by the one or more recording electrodes 1. The wireless communication module 6 may analyze the neural data communicated by the first internal pulse generator 3.

The wireless communication module 6 may also be in communication with the second internal pulse generator 5. The communication may be wireless, wired, and or through various communication protocols such as IR, Bluetooth, UV etc. The wireless communication module 6 may communicate stimulation instructions to the second internal pulse generator 5. The stimulation instructions may include a desired stimulation protocol to be delivered via the one or more stimulating electrodes 4.

The stimulation instructions may depend on the characteristics of the neural data communicated by the first internal pulse generator 3 to the wireless communication module 6. For instance, the wireless communication module 6 may analyze the neural data communicated by the first internal pulse generator 3 for characteristics that can be used to modulate the VNS therapy. Such characteristics may include the phase amplitude cross frequency coupling, cross frequency coherence, frequency coupling and coherence across one or more electrode channels, and or phase coupling and coherence across one or more electrode channels. Additional characteristics are discussed in connection with FIG. 2. The wireless communication module 6 may then communicate a stimulation protocol based on the neural data's characteristics to the second internal pulse generator 5 to modulate the application of VNS.

The one or more stimulating electrodes 4 may be configured to receive stimulation instructions from the second internal pulse generator 5, and to deliver stimulation to the vagus nerve. The one or more stimulating electrodes 4 may be a variety of forms. As one example, the one or more stimulating electrodes 4 may include a cuff electrode that wraps around the surface of the vagus nerve. In another example, the one or more stimulating electrodes 4 may include a transverse penetrating electrode that punctures the cellular membrane of the vagus nerve. The one or more stimulating electrodes 4 may be formed according to the process described above with respect to the one or more recording electrodes 1.

Any of the features, components, parts, including the arrangements and configurations thereof shown in FIG. 1 can be included, either alone or in any combination, in any of the other examples of devices, features, components, and parts shown in the other figures. Likewise, any of the features, components, parts, including the arrangements and configurations thereof shown in the other figures can be included, either alone or in any combination, in the example of the devices, features, components, and parts shown in FIG. 1.

Figure 2:
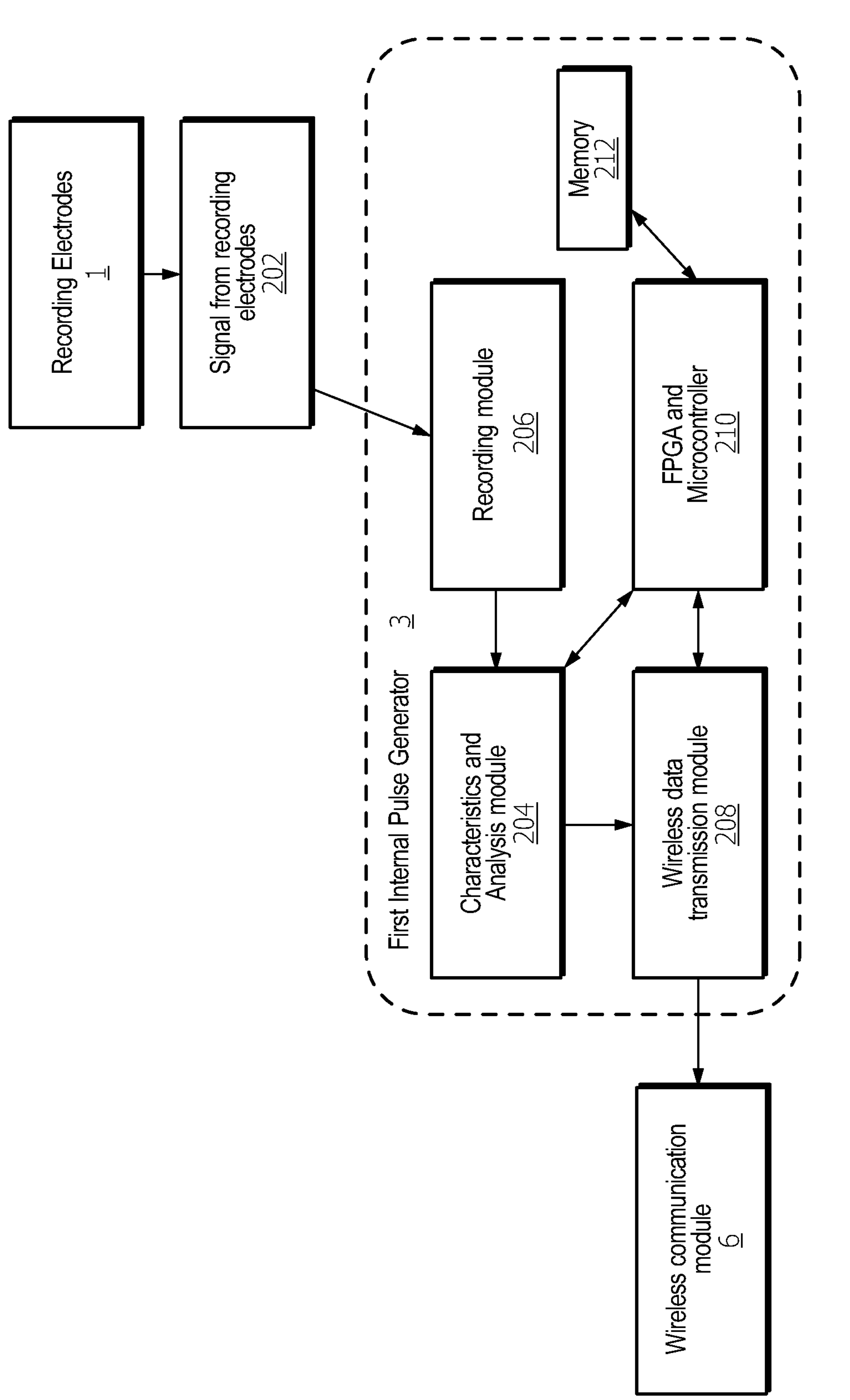
FIG. 2 illustrates a block diagram of one embodiment of an internal pulse generator.

FIG. 2 illustrates a block diagram of an embodiment of the first internal pulse generator 3 described in connection with FIG. 1. As described above, the first internal pulse generator 3 may be in communication with the one or more recording electrodes 1. The one or more recording electrodes 1 may record field potentials produced by neurological tissue in proximity to the one or more recording electrodes and communicate those recorded field potentials to the first internal pulse generator 3. A recording module 206 in the first internal pulse generator 3 may be configured to receive the field potential recordings (e.g., signals 202) from the one or more recording electrodes 1. The recording module 206 may include a system on a chip capable of recording the neurological signals from the one or more recording electrodes 1.

The first internal pulse generator 3 may include a characteristics and analysis module 204. The recording module 206 may be in communication with the characteristics and analysis module 204, and the characteristics and analysis module 204 may be configured to receive recorded field potentials (e.g., signals 202) from the recording module 206. The characteristics and analysis module 204 may be configured to analyze the recorded field potentials from the recording module 206 to determine one or more brain states. In some examples, a characteristics and analysis module includes one or more processors. Additionally or alternatively, a characteristics and analysis module includes computer-executable instructions that, when executed by the one or more processors, causes an internal pulse generator to perform the various operations described herein. In certain implementations, a characteristics and analysis module includes one or more neural networks trained on field potentials (or other neurological signals) and ground truth data (e.g., brain states) associated with such field potentials.

In one example, the characteristics and analysis module 204 may be configured to analyze the recorded neurological signals using EEG spectral analysis. In this example, a Hilbert transform may be used to analyze the instantaneous and near-instantaneous power in a recorded EEG signals at different frequency bands. These frequency bands may include delta (<4 Hz), theta (4-8 Hz), alpha (8-12 Hz), beta (12-30 Hz), gamma (30-80 Hz), high-gamma (>80 Hz). If necessary these recorded EEG signals may be normalized using known techniques. These recorded signals may be analyzed to determine the relative mean power as a percentage decrease or increase of mean power relative to a baseline, the ratios of mean power between any two spectral power bands (e.g. gamma band power divided by alpha band power, gamma band power divided by theta band power, etc.), and the differential power ratios in certain frequency bands across the one or more recording electrodes (the difference between the gamma band power between the one or more recording electrodes, etc.). This analysis may provide indicators of specific brain states, which can be used to determine whether a VNS protocol should be administered, and or to modulate the VNS stimulation protocol to either increase or decrease the amplitude, frequency, pulse width, duty cycle, mode (e.g. tonic high frequency, theta-burst), or duration of the VNS stimulation.

Example 1: Determine the effects of imposed hyperventilation. Specifically, if the characteristics and analysis module 204 determines that the alpha-band power or the gamma-band power is significantly reduced during the period of hyperventilation, then the characteristics and analysis module 204 can maintain or increase the amplitude of the VNS stimulation. By contrast, if the characteristics and analysis module 204 determines that the alpha-band power has not changed during the period of hyperventilation, then the characteristics and analysis module 204 can either decrease the amplitude of the VNS stimulation or turn off the VNS stimulation altogether.

Example 2: Determine the effects of intermittent photic stimulation (e.g., light flickering at 2-60 Hz). For instance, if the characteristics and analysis module 204 determines that the gamma-band power is significantly reduced during the period of photic stimulation, then the characteristics and analysis module 204 can maintain or increase the amplitude of the VNS stimulation. By contrast, if the characteristics and analysis module 204 determines that the gamma-band power is not changed during the period of photic stimulation, then the characteristics and analysis module 204 can either decrease the amplitude of the VNS stimulation or turn off the VNS stimulation for a period of time (e.g., for 1 hour).

Example 3: Measure the pair-wise derived brain symmetry values (pdBSI) for the delta, theta, alpha and beta bands. Note that the characteristics and analysis module 204 can measure the pdBSI using homologous electrode channel pairs. A lower pdBSI indicates more symmetry across the homologous channel pairs of the two hemispheres. Thus, if the characteristics and analysis module 204 determines that the theta-band pdBSI falls below a given threshold value, then the characteristics and analysis module 204 can increase the amplitude of the VNS stimulation. By contrast, if the characteristics and analysis module 204 determines that the theta-band pdBSI stays above a threshold value, then the characteristics and analysis module 204 can either maintain the VNS amplitude, reduce the amplitude by a predetermined amount (e.g., 50%), or turn off the VNS stimulator for a period of time (e.g., 1 hour).

Example 4: If the characteristics and analysis module 204 determines the global power in the theta and alpha band is reduced during a standard-cycle VNS (e.g., 30 s on, 300 s off) and rapid-cycle VNS (e.g., 7 s on, 18 s off) compared to when the VNS is turned off, then the characteristics and analysis module 204 can cause the continuation of the VNS stimulation at the same amplitude. However, if the characteristics and analysis module 204 determines that the global power in the theta and alpha band is not reduced, then the characteristics and analysis module 204 can turn off the VNS stimulation for a period of time (e.g., 1 hour).

Example 5: If the characteristics and analysis module 204 determines that the global power in the gamma frequency band falls below a defined threshold value, then the characteristics and analysis module 204 can either maintain or increase the VNS stimulation amplitude. However, if the characteristics and analysis module 204 determines that the global power in the gamma band does not decrease in response to the VNS stimulation, then the characteristics and analysis module 204 can cause the VNS stimulation to turn off for a period of time (e.g., 1 hour).

In yet another embodiment, the characteristics and analysis module 204 may be configured to analyze recorded field potentials for temporal shifts in the field potentials as they propagate across different brain regions. For example, the one or more recording electrodes 1 may record field potentials at different times and at different neurological tissue locations. Each of these recorded field potentials may be compared with one another to determine a temporal shift in recorded field potentials as they propagate across many brain regions at different times.

To illustrate a particular example of temporal shift analysis, the characteristics and analysis module 204 can implement one or more of the modulation triggering mechanisms described in Examples 1-5 above whereby an effect is first observed in brain region A (e.g. the left temporal cortex) followed within a certain time interval (e.g. seconds or minutes) by the same or different effect (see Example 1-5 above) observed in brain region B (e.g. prefrontal cortex or parietal cortex). Such a temporal shift analysis can be performed for myriad different neurological conditions, such as focal epilepsy with a seizure onset zone in the temporal lobe (hippocampal region).

In another example, the characteristics and analysis module 204 may be configured to analyze the recorded field potentials for field potentials elicited by VNS (i.e. vagal evoked potentials) to determine one or more brain states. Vagal evoked potentials are compound waveforms with several phases. The early phase of a vagal evoked potential is elicited approximately 5-70 milliseconds post VNS stimulation, the immediate phase is elicited approximately 70-250 milliseconds post VNS stimulation, and the late phase is elicited 250-700 milliseconds post VNS stimulation. These vagal evoked potentials may be modulated by the brain state of the patient and their ongoing cortico-thalamic activity at the time the VNS stimulation is delivered. Each of these vagal evoked potential phases may have aspects that can be analyzed by the characteristics and analysis module 204. These aspects may include peak amplitude, peak-to-trough amplitude, root-mean-square power, and ratios of any combination of these measures across the one or more recording electrodes. This analysis may provide indicators of specific brain states, which can be used to determine whether a VNS protocol should be administered, and or to modulate the VNS stimulation protocol to either increase or decrease the amplitude, frequency, pulse width, duty cycle, mode (e.g. tonic high frequency, theta-burst), or duration of the VNS stimulation.

In yet another example, the one or more brain states generated from the characterizations of the recorded field potentials by the characteristics and analysis module 204 may be used to modulate a VNS stimulation protocol. For example, if a vagal evoked response to a VNS stimulation is above a desired characteristics threshold (e.g. peak amplitude above a desired peak amplitude), the VNS stimulation may be decreased in power. Alternatively, if a vagal evoked response to a VNS stimulation is below a desired characteristics threshold (e.g. peak-to-trough amplitude is below a desired amount), the VNS stimulation may be modified to increase the peak-to-trough amplitude. Each of the above described characteristics of the recorded field potentials, in combination or in isolation, can be used to modify the VNS stimulation protocol to improve the therapeutic effects of VNS therapy.

In other terms, the characteristics and analysis module 204 may identify a particular vagal evoked response for a particular region of a brain. In response, the characteristics and analysis module 204 can titrate or calibrate the VNS energy delivered to the entire brain based on the vagal evoked potential recorded in a specific region. For example, if large VEPs are detected (as is often the case in NREM sleep), the VNS stimulator program could be adjusted to reduce the duty cycle (i.e. have shorter ON periods) in order to have less of an effect on the patient's sleep cycles.

The characteristics and analysis module 204 may be in communication with a field programmable gate array and microcontroller 210. The characteristics and analysis module 204 may be configured to transmit the characteristics of the recorded neural data to the field programmable gate array and microcontroller 210. The field programmable gate array and microcontroller 210 may also be in communication with a memory 212.

The characteristics and analysis module 204 may be in communication with a field programmable gate array and microcontroller 210. The characteristics and analysis module 204 may be configured to transmit the characteristics of the recorded neural data to the field programmable gate array and microcontroller. The field programmable gate array and microcontroller 210 may also be in communication with the memory 212.

The characteristics and analysis module 204 and the field programmable gate array and microcontroller 210 may be in communication with a wireless data transmission module 208. The wireless data transmission module 208 may also be in communication with the wireless communication module 6. The wireless data transmission module 208 may transmit the characteristics of the neural data from the characteristics and analysis module 204 to the wireless communication module 6. The wireless data transmission module 208 may transmit the characteristics of the neural data received from the field programmable gate array and microcontroller 210 to the wireless communication module 6.

Any of the features, components, parts, including the arrangements and configurations thereof shown in FIG. 2 can be included, either alone or in any combination, in any of the other examples of devices, features, components, and parts shown in the other figures. Likewise, any of the features, components, parts, including the arrangements and configurations thereof shown in the other figures can be included, either alone or in any combination, in the example of the devices, features, components, and parts shown in FIG. 2.

Figure 3:
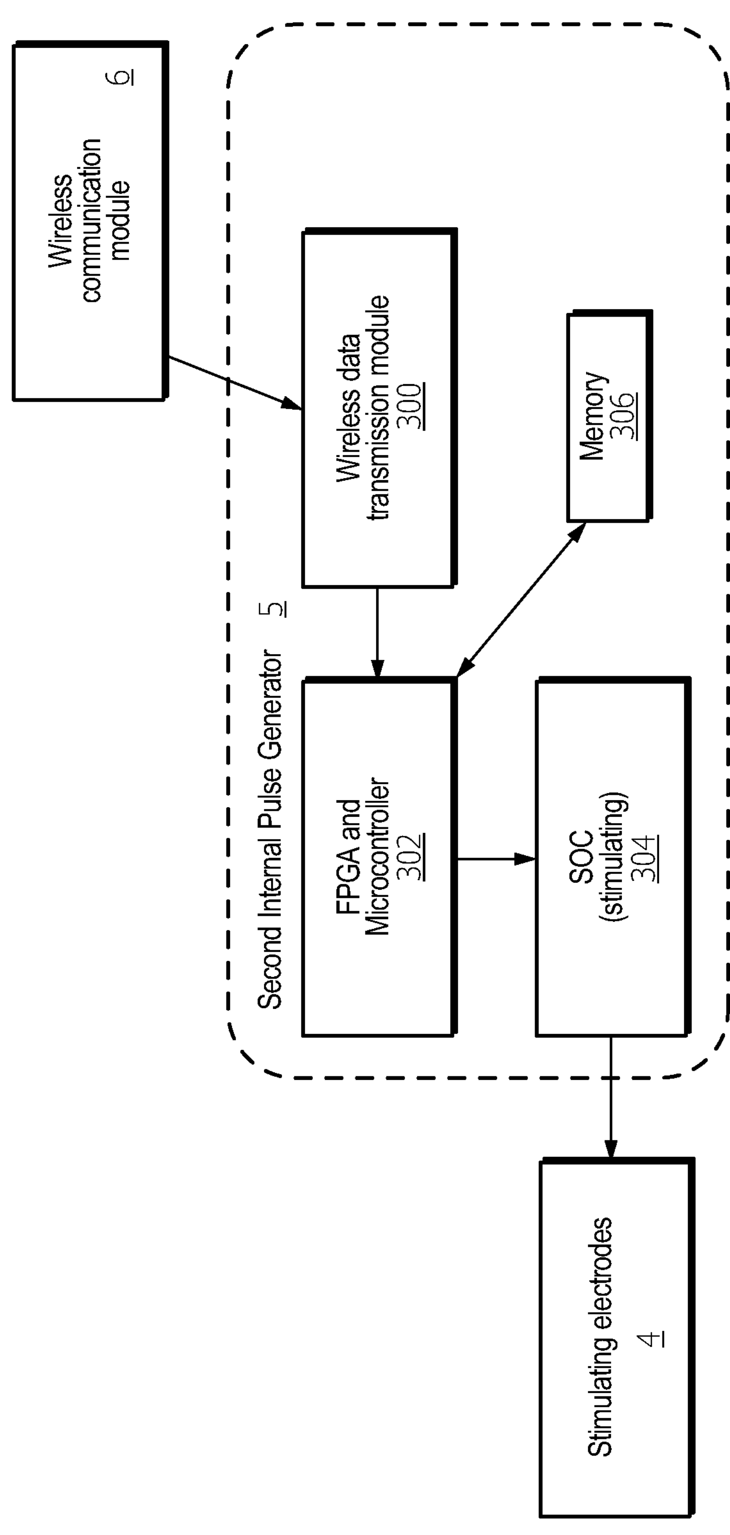
FIG. 3 illustrates a block diagram of a second embodiment of an internal pulse generator.

FIG. 3 illustrates a block diagram of an embodiment of the second internal pulse generator 5 described in connection with FIG. 1. As described above, the second internal pulse generator 5 may be in communication with the wireless communication module 6. The second internal pulse generator 5 may include a wireless data transmission module 300 in order to communicate with the wireless communication module 6.

The wireless data transmission module 300 may be configured to receive a stimulation protocol from the wireless communication module 6. The wireless data transmission module 300 may be in communication with a field programmable gate array and microcontroller 302. The field programmable gate array and microcontroller 302 may be configured to receive the stimulation protocol instructions from the wireless data transmission module 300.

The field programmable gate array and microcontroller 302 may be in communication with a memory 306. The field programmable gate array and microcontroller 302 may be in communication with a system on a chip 304 capable of generating a stimulation protocol. The system on chip 304 may be in communication with the one or more stimulating electrodes 4. The system on chip 304 may deliver the stimulation protocol to the one or more stimulating electrodes 4, thereby stimulating the vagus nerve.

Any of the features, components, parts, including the arrangements and configurations thereof shown in FIG. 3 can be included, either alone or in any combination, in any of the other examples of devices, features, components, and parts shown in the other figures. Likewise, any of the features, components, parts, including the arrangements and configurations thereof shown in the other figures can be included, either alone or in any combination, in the example of the devices, features, components, and parts shown in FIG. 3.

Figure 4:
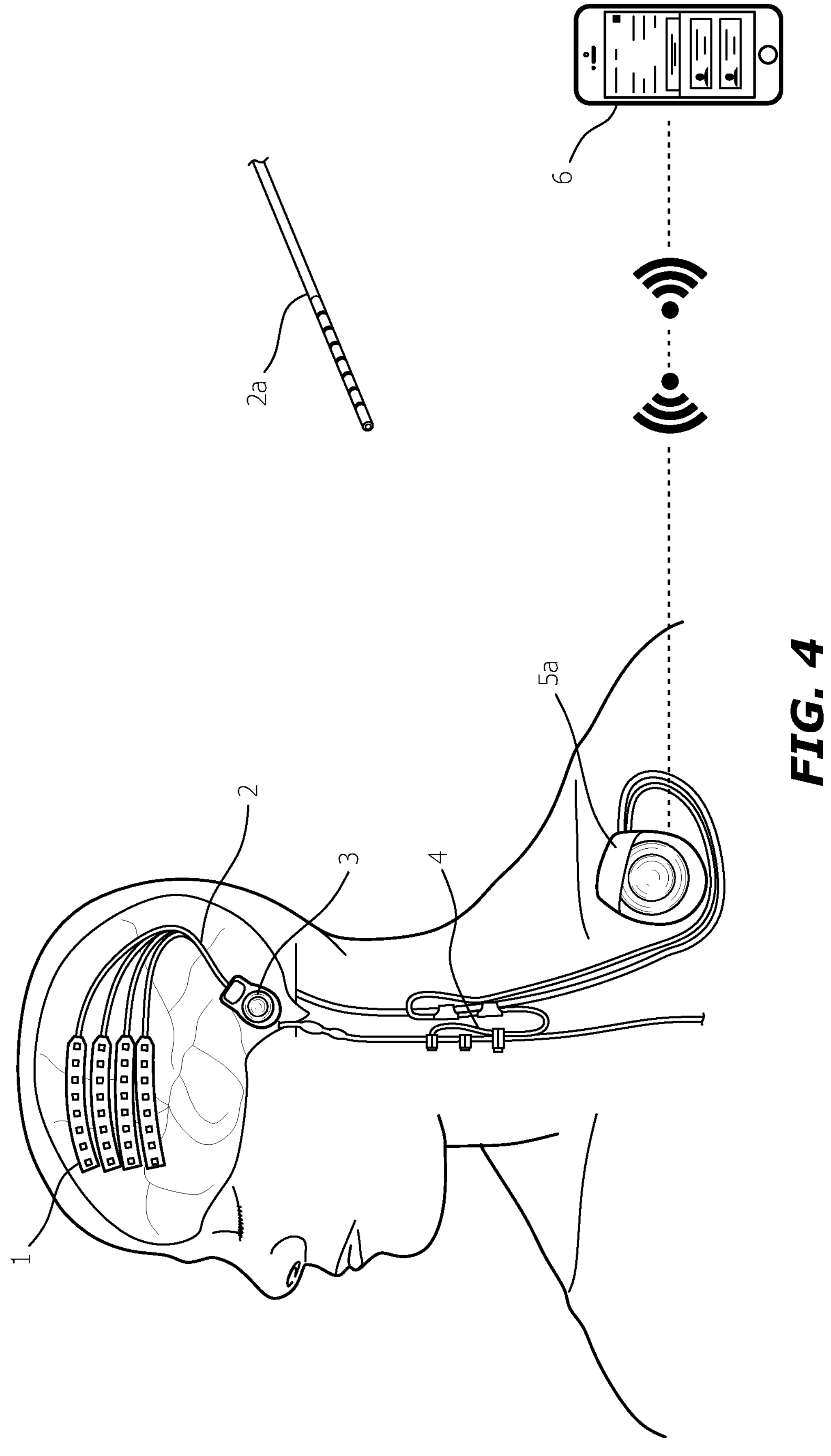
FIG. 4 illustrates a diagram of a second embodiment of a medical implant system that can be used for vagus nerve stimulation therapy.

FIG. 4 illustrates a diagram of a second embodiment of a medical implant system that can be used for VNS. The embodiment includes an internal pulse generator 5*a*; the wireless communication module 6 in communication with the internal pulse generator 5*a*; one or more recording electrodes 1 in communication with the internal pulse generator 5*a*, wherein the one or more recording electrodes 1 are configured to record field potentials produced by neural tissue in proximity to the one or more recording electrodes 1; one or more stimulating electrodes 4 in communication with the internal pulse generator 5*a*, wherein the one or more stimulating electrodes 4 are configured to stimulate the vagus nerve.

The one or more recording electrodes 1 may be implanted in a patient in a subdural location, implanted in the subgaleal space of a patient, and or placed on a patient's scalp using an EEG cap. The one or more recording electrodes 1 can be formed by one or more layers of electrically conducting material and/or electrically insulating material jointly forming electrical access sites. In some embodiments, the one or more recording electrodes 1 can include at least two layers of insulating material and at least one layer of electrically conducting material. In some embodiments, the one or more recording electrodes 1 can be formed with a first electrically insulating layer and a second electrically insulating layer encapsulating an electrically conducting layer sandwiched between the first electrically insulating layer and the second electrically insulating layer. The first insulating layer and/or the second insulating layer can be configured to include openings that permit access to the electrically conducting layer forming the electrical access sites.

In some embodiments, the electrically insulating layers and/or the electrically conducting layer can be formed via deposition of material. For example, in some embodiments, at least one layer of insulating material (e.g., the first electrically insulating layer or the second electrically insulating layer) can serve as a substrate and base layer for all other material layers (e.g., one or more electrically conducting layers, one or more additional electrically insulating layers, etc.) deposited on top of this base layer. In some embodiments, the electrically conducting layer can be patterned to create conducting leads/traces between electrode access sites and a connector interface, as described herein. The electrically conducting layer may be used to electrically couple to and provide access to multiple electrode access sites. In some embodiments, the electrode access sites may include one or more additional electrically conducting layers that may provide additional electrically conducting traces.

In some such embodiments, there may be at least one insulating material layer that encloses each of the electrically conducting layers or electrically conducting traces, electrically insulating the different electrically conductive traces and electrode sites from one another, as well as from the biological environment. In some embodiments, the electrically insulating layer can be patterned to expose (1) the electrode sites at the distal extremity of the electrode array to biological tissue and biological fluids for charge transfer and (2) the bond sites at the proximal extremity of the electrode array serving as interface to the connector.

In some embodiments, the material for forming the electrically insulating layers can be selected based on one or more specific criteria including biocompatible molecular composition, high electrical capacitance, low thermal conductivity and thermal mass, low areal mass density, defect-free, thermal and chemical compatibility with polymer substrates and stability in electrolyte solutions at physiological pH and temperature.

In some embodiments, the electrically insulating layers can be formed from any suitable material including silicone, polyurethane, polyimide, silicon carbide, SU-8, a liquid crystal polymer (LCP), Parylene-C, a ceramic, silicon dioxide, or any combination thereof. The electrically insulating layer can be of any suitable thickness and can be fabricated or formed using any suitable process. For example, in some embodiments, the electrically insulating layer can be formed from an ultrathin layer of thermal silicon oxide which can be transfer bonded.

In some embodiments, the electrically conducting layer can be made from any suitable material including gold, platinum, iridium, iridium oxide, titanium nitride, poly(3,4-ethylenedioxythiophene (PEDOT), PEDOT-PSS (PolyStyrene Sulfonate), carbon nano-tubes (CNT), or a combination of these materials in form of alloys or material stacks. The electrically conducting layer can be of any suitable thickness and can be fabricated or formed using any suitable process.

The electrically conducting layer can be configured to include electrode access sites that can be arranged in any suitable pattern across the one or more recording electrodes 1. In some embodiments, the electrode access sites can be situated or formed specifically in an area such that there is a desired distance between the two most distant electrode access sites. The desired distance between the two most distant electrode access sites can be any suitable distance based on the application that the device can be used for. For example, the distance can be approximately 1 mm to approximately 50 mm including any measure of distance therebetween. The one or more recording electrodes 1 can be formed to assume any number of geometric shapes that can enable precise recording of electrical activity. In some implementations, the one or more recording electrodes 1 can be chosen to be of a particular shape dependent on the geometric shape of the target tissue and tissue surrounding it. In some implementations, the shape of the one or more recording electrodes 1 can be chosen based on the access to the target tissue for example one or more insertion sites, and/or dependent on the particular recording application desired.

As an example, the electrode access sites may be arranged according to any suitable pattern including a linear pattern, a circular pattern, an array pattern, or any other desired or customized pattern. The electrode access sites may be configured in rows (i.e. 1 row of 8 electrode access sites, 1 row of 4 electrode access sites, 2 rows of 2 electrode access sites, 4 rows of 4 electrode access sites. The number of electrode access sites per the one or more recording electrodes 1 may range between 1 and 64 sites.

The electrode access sites on the one or more recording electrodes 1 may be connected to one or more cables 2. The one or more cables 2 may be subcutaneous implanted. The one or more cables 2 may include a plurality of leads, where each lead may be connected to an electrode access site in a manner that is electrically insulated from other electrode access sites on the one or more recording electrodes 1. Each insulated electrode access site and cable lead pair may be described as a channel. The one or more cables 2 may include one or more terminating pigtail channel connectors 2*a*. The one or more terminating pigtail channel connectors 2*a* may connect one or more channels to the internal pulse generator 5*a*. The one or more terminating pigtail channel connectors 2*a* may connect a plurality of 8 channels, or 16 channels to the first internal pulse generator 5*a*. For example, four 16 channel pigtail channel connectors 2*a* may connect 64 channels to the first internal pulse generator.

The one or more recording electrodes 1 can be configured to be capable of recording field potentials, EEG signals, and or action potentials. In some embodiments, the recorded local field potentials may be characterized, and this characterization is discussed in more detail in connection with FIG. 5 below.

The internal pulse generator 5*a* is described more fully in connection with FIG. 5 below. The internal pulse generator 5*a* may be in communication with the wireless communication module 6. The communication may be wireless or wired. Some particular examples of wireless communication include a Wi-Fi based communication, mesh network communication, BlueTooth® communication, near-field communication, low-energy communication, Zigbee communication, Z-wave communication, and 6LoWPAN communication. Other forms of communication include wired connections, such as a USB connection, UART connection, USART connection, I2C connection, SPI connection, QSPI connection, etc. The internal pulse generator 5*a* may communicate to the wireless communication module 6 neural data obtained by the one or more recording electrodes 1. The wireless communication module 6 may analyze the neural data communicated by the internal pulse generator 5*a*.

The wireless communication module 6 may communicate stimulation instructions to the internal pulse generator 5*a*. The stimulation instructions may include a desired stimulation protocol to be delivered via the one or more stimulating electrodes 4.

The stimulation instructions may depend on the characteristics of the neural data communicated by the internal pulse generator 5*a* to the wireless communication module 6. For instance, the wireless communication module 6 may analyze the neural data communicated by the internal pulse generator 5*a* for characteristics that indicate an impending seizure state. The wireless communication module 6 may then communicate a stimulation protocol based on the neural data's characteristics to the internal pulse generator 5*a* in order to stimulate the one or more stimulating electrodes 4.

The one or more stimulating electrodes 4 may be configured to receive stimulation instructions from the internal pulse generator 5*a*, and to deliver stimulation to the vagus nerve. The one or more stimulating electrodes 4 may be a variety of forms. As one example, the one or more stimulating electrodes 4 may include a cuff electrode that wraps around the surface of the vagus nerve. In another example, the one or more stimulating electrodes 4 may include a transverse penetrating electrode that punctures the cellular membrane of the vagus nerve. The one or more stimulating electrodes 4 may be formed according to the process described above with respect to the one or more recording electrodes 1.

Any of the features, components, parts, including the arrangements and configurations thereof shown in FIG. 4 can be included, either alone or in any combination, in any of the other examples of devices, features, components, and parts shown in the other figures. Likewise, any of the features, components, parts, including the arrangements and configurations thereof shown in the other figures can be included, either alone or in any combination, in the example of the devices, features, components, and parts shown in FIG. 4.

Figure 5:
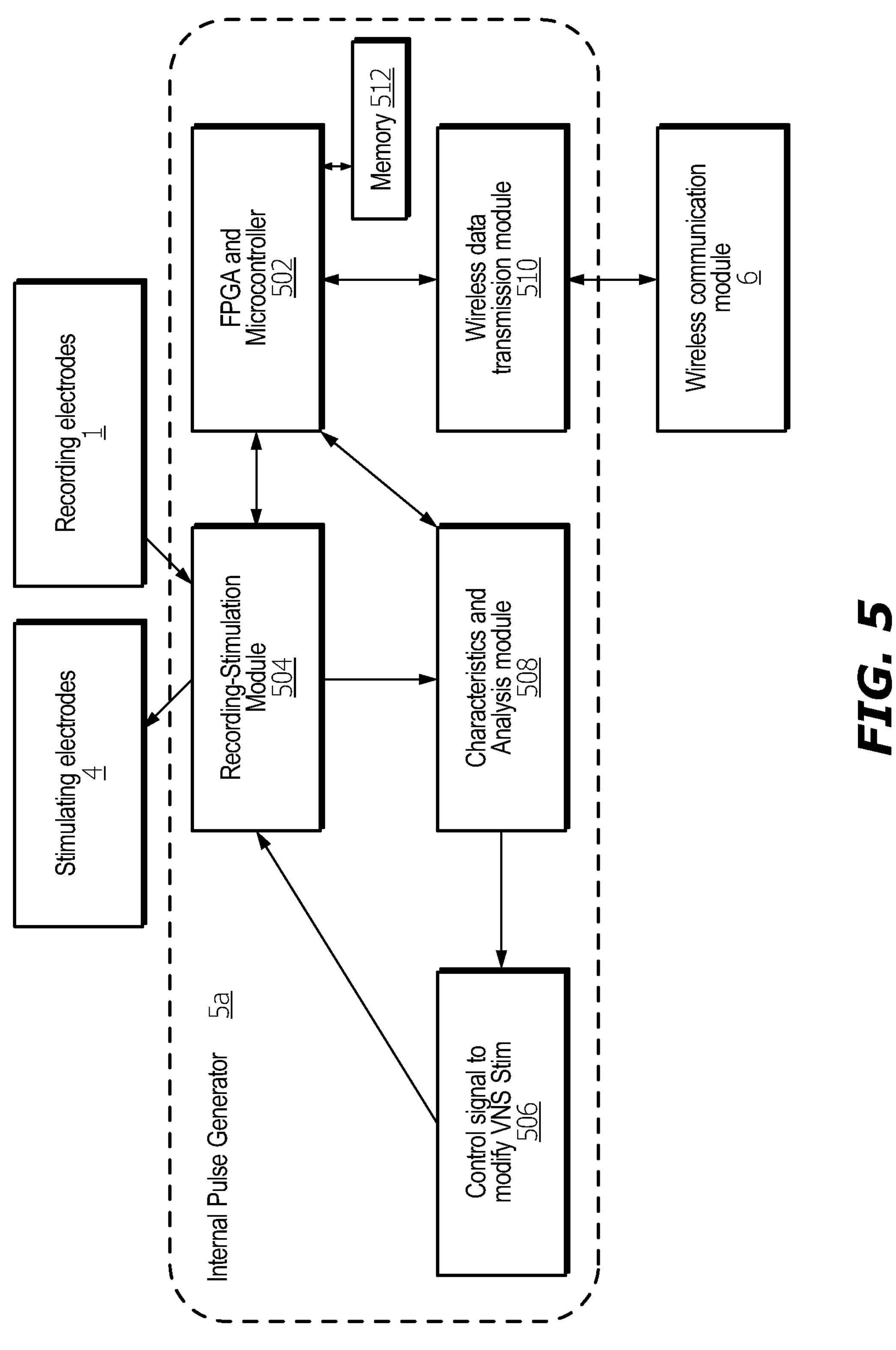
FIG. 5 illustrates a block diagram of the internal pulse generator of FIG. 4.

FIG. 5 illustrates a block diagram of the internal pulse generator 5*a* of FIG. 4. As described above, the internal pulse generator 5*a* may be in communication with the one or more recording electrodes 1. The one or more recording electrodes 1 may record field potentials produced by neural tissue in proximity to the one or more recording electrodes 1 and send those recorded field potentials to the internal pulse generator 5*a* via the one or more cables 2. A recording-stimulation module 504 in the internal pulse generator 5*a* may be configured to receive the recorded field potentials from the one or more recording electrodes 1. The recording-stimulation module 504 may include a system on a chip capable of recording the neurological signals from the one or more recording electrodes 1. The system on chip of the recording-stimulation module 504 can also generate stimulation signals for providing to the stimulating electrodes 4 (as discussed below).

The internal pulse generator 5*a* may include a characteristics and analysis module 508 (which may be the same as or similar to the characteristics and analysis module 204 described above). The recording-stimulation module 504 may be in communication with the characteristics and analysis module 508, and the characteristics and analysis module 508 may be configured to receive recorded field potentials from the recording module 504. The characteristics and analysis module 508 may be configured to analyze the recorded field potentials from the recording-stimulation module 504 for characteristics.

In one example, the characteristics and analysis module 508 may be configured to analyze the recorded field potentials using EEG spectral analysis. In this example, a Hilbert transform may be used to analyze the instantaneous and near-instantaneous power in a recorded EEG signals at different frequency bands. These frequency bands may include delta (<4 Hz), theta (4-8 Hz), alpha (8-12 Hz), beta (12-30 Hz), gamma (30-80 Hz), high-gamma (>80 Hz). If necessary these recorded EEG signals may be normalized using known techniques. These recorded signals may be analyzed to determine the relative mean power as a percentage decrease or increase of mean power relative to a baseline, the ratios of mean power between any two spectral power bands (e.g. gamma band power divided by alpha band power, gamma band power divided by theta band power, etc.), and the differential power ratios in certain frequency bands across the one or more recording electrodes (the difference between the gamma band power between the one or more recording electrodes, etc.). This analysis may provide indicators of specific brain states, which can be used to determine whether a VNS protocol should be administered, and or to modulate the VNS stimulation protocol to either increase or decrease the amplitude, frequency, pulse width, duty cycle, mode (e.g. tonic high frequency, theta-burst), or duration of the VNS stimulation. Some examples (e.g., Examples 1-5) are provided above.

In another example, the characteristics and analysis module 508 may be configured to analyze the recorded field potentials for field potentials elicited by VNS (i.e. vagal evoked potentials) to determine one or more brain states. Vagal evoked potentials are compound waveforms with several phases. The early phase of a vagal evoked potential is elicited approximately 5-70 milliseconds post VNS stimulation, the immediate phase is elicited approximately 70-250 milliseconds post VNS stimulation, and the late phase is elicited 250-700 milliseconds post VNS stimulation. These vagal evoked potentials may be modulated by the brain state of the patient and their ongoing cortico-thalamic activity at the time the VNS stimulation is delivered. Each of these vagal evoked potential phases may have aspects that can be analyzed by the characteristics and analysis module 508. These aspects may include peak amplitude, peak-to-trough amplitude, root-mean-square power, and ratios of any combination of these measures across the one or more recording electrodes. This analysis may provide indicators of specific brain states, which can be used to determine whether a VNS protocol should be administered, and or to modulate the VNS stimulation protocol to either increase or decrease the amplitude, frequency, pulse width, duty cycle, mode (e.g. tonic high frequency, theta-burst), or duration of the VNS stimulation, in a same or similar manner as described above.

In yet another embodiment, the characteristics and analysis module 508 may be configured to analyze recorded field potentials for temporal shifts in the field potentials as they propagate across different brain regions. For example, the one or more recording electrodes 1 may record field potentials at different times and at different neurological tissue locations. Each of these recorded field potentials may be compared with one another to determine a temporal shift in recorded field potentials as they propagate across many brain regions at different times.

In yet another example, the one or more brain states generated from the characterizations of the recorded field potentials by the characteristics and analysis module 508 may be used to modulate a VNS stimulation protocol (e.g., via a control signal 506). For example, if the characteristics of one or more brain states is above a desired characteristics threshold (e.g. peak amplitude above a desired peak amplitude), the characteristics and analysis module 508 may transmit a control signal 506 to the recording-stimulation module 504 to decrease the VNS stimulation in power. Alternatively, if the one or more brain states is below a desired characteristics threshold (e.g. peak-to-trough amplitude is below a desired amount), the characteristics and analysis module 508 may transmit a control signal 506 to the recording-stimulation module 504 to increase the VNS stimulation in the peak-to-trough amplitude. Each of the above described characteristics of the recorded field potentials, in combination or in isolation, can be used to modify the VNS stimulation protocol to improve the therapeutic effects of VNS therapy.

The characteristics and analysis module 508 may be in communication with a field programmable gate array and microcontroller 502. The characteristics and analysis module 508 may be configured to transmit the characteristics of the recorded neural data to the field programmable gate array and microcontroller 502. The field programmable gate array and microcontroller 502 may also be in communication with a memory 512.

The characteristics and analysis module 508 and the field programmable gate array and microcontroller 502 may be in communication with a wireless data transmission module 510. The wireless data transmission module 510 may also be in communication with the wireless communication module 6. The wireless data transmission module 510 may transmit the characteristics of the neural data from the characteristics and analysis module 508 to the wireless communication module 6. The wireless data transmission module 510 may transmit the characteristics of the neural data received from the field programmable gate array and microcontroller 502 to the wireless communication module 6.

The wireless data transmission module 510 may be configured to receive a stimulation protocol from the wireless communication module 6. The field programmable gate array and microcontroller 502 may be configured to receive the stimulation protocol instructions from the wireless data transmission module 510. The field programmable gate array and microcontroller 502 may be in communication with a system on a chip of the recording-stimulation module 504 capable of generating a stimulation protocol. The system on a chip may be in communication with the one or more stimulating electrodes 4. The system on a chip may deliver the stimulation protocol to the one or more stimulating electrodes 4, thereby stimulating the vagus nerve.

Any of the features, components, parts, including the arrangements and configurations thereof shown in FIG. 5 can be included, either alone or in any combination, in any of the other examples of devices, features, components, and parts shown in the other figures. Likewise, any of the features, components, parts, including the arrangements and configurations thereof shown in the other figures can be included, either alone or in any combination, in the example of the devices, features, components, and parts shown in FIG. 5.

Figure 6:
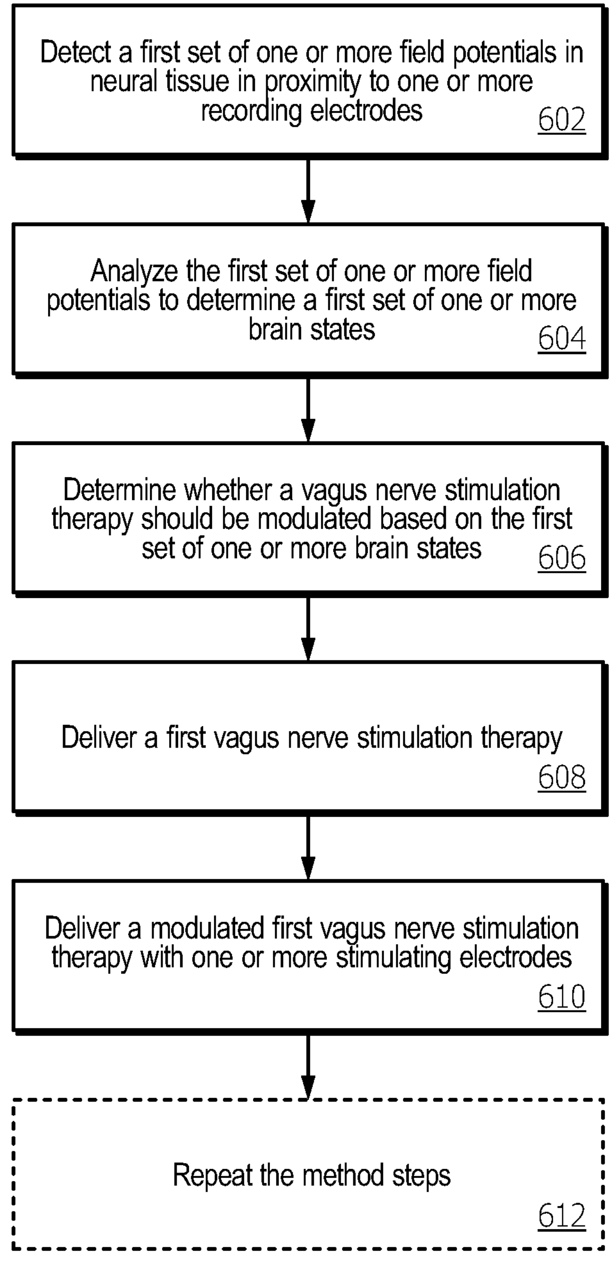
FIG. 6 illustrates a block diagram of method steps for applying a vagus nerve stimulation therapy.

Yet another example of the present disclosure also relates to a method of treating a neurological disorder. In accordance with one or more embodiments of the present disclosure, FIG. 6 illustrates a method of treating a neurological disorder. As shown in FIG. 6, the method includes a step 202 of detecting a first set of local field potentials in neural tissue in proximity to one or more recording electrodes; a step 605 of analyzing (e.g., characterizing) from the first set of one or more local field potentials, a first set of one or more brain states; a step 606 of determining whether the first set of one or more brain states is indicative of a neurological disorder suitable for vagus nerve stimulation therapy; a step 608 of delivering a first vagus nerve stimulation therapy with one or more stimulating electrodes; a step 610 of following the first vagus nerve stimulation therapy, delivering a modulated first vagus nerve stimulation therapy with one or more stimulating electrodes. To do so, the step 610 can include: detecting a second set of one or more local field potentials in neural tissue in proximity to one or more recording electrodes; identifying from the second set of one or more local field potentials a second set of one or more brain states; and comparing the first set of one or more brain states and the second set of one or more brain states to determine if a brain state indicative of a neurological disorder persists. If the neurological disorder persists (or if certain neurological signals are still present) a step 612 may be performed to repeat the foregoing steps (e.g., by utilizing the characteristics and analysis module 508 to modify the VNS stimulation).

Some embodiments of the apparatuses and methods described herein can be used for in-vivo implementations, i.e., to interface with a neural system of a live organism. Some embodiments of the apparatuses and methods described herein can be used to interface with a neural system of a live organism that is awake and performing a behavior.

It will be appreciated that the method steps illustrated and described in conjunction with FIG. 6 can be modified, added to, or omitted in one or more embodiments. Indeed, any of the method steps and corresponding features, components, parts, arrangements, and configurations thereof shown in FIG. 6 can be included, either alone or in any combination, in any of the other examples of devices, features, components, and parts shown in the other figures. Likewise, any of the features, components, parts, including the arrangements and configurations thereof shown in the other figures can be included, either alone or in any combination, in the example method steps shown in FIG. 6.

As used in this specification, the singular forms “a,” “an,” and “the” include plural referents unless the context clearly dictates otherwise. Thus, for example, the term “a member” is intended to mean a single member or a combination of members, "a material" is intended to mean one or more materials, or a combination thereof.

The term "substantially" when used in connection with "cylindrical," "linear," and/or other geometric relationships is intended to convey that the structure so defined is nominally cylindrical, linear or the like. As one example, a portion of a support member that is described as being "substantially linear" is intended to convey that, although linearity of the portion is desirable, some non-linearity can occur in a "substantially linear" portion. Such non-linearity can result from manufacturing tolerances, or other practical considerations (such as, for example, the pressure or force applied to the support member). Thus, a geometric construction modified by the term "substantially" includes such geometric properties within a tolerance of plus or minus 5% of the stated geometric construction. For example, a "substantially linear" portion is a portion that defines an axis or center line that is within plus or minus 5% of being linear.

As used herein, the term "set" and "plurality" can refer to multiple features or a singular feature with multiple parts. For example, when referring to a set of electrodes, the set of electrodes can be considered as one electrode with multiple portions, or the set of electrodes can be considered as multiple, distinct electrodes. Additionally, for example, when referring to a plurality of electrochemical cells, the plurality of electrochemical cells can be considered as multiple, distinct electrochemical cells or as one electrochemical cell with multiple portions. Thus, a set of portions or a plurality of portions may include multiple portions that are either continuous or discontinuous from each other. A plurality of particles or a plurality of materials can also be fabricated from multiple items that are produced separately and are later joined together (e.g., via mixing, an adhesive, or any suitable method).

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A medical implant system comprising:

an internal pulse generator including a wireless data transmission module;

a wireless communication module in communication with the wireless data transmission module of the internal pulse generator;

one or more recording electrodes in communication with the internal pulse generator;

wherein the one or more recording electrodes are configured to monitor to detect one or more field potentials produced by neural tissue in proximity to the one or more recording electrodes, the one or more field potentials including neural data, wherein the wireless data transmission module is configured to transmit the neural data to the wireless communication module, wherein the wireless communication module is configured to modify a stimulation protocol based on the neural data and to transmit the modified stimulation protocol to the wireless data transmission module; and one or more stimulating electrodes in communication with the internal pulse generator;

wherein the one or more stimulating electrodes are configured to stimulate the vagus nerve according to the modified stimulation protocol.

2. The medical implant system of claim 1, wherein the internal pulse generator is comprised of:

a system on a chip capable of stimulating and recording neurological tissue;

a field programmable gate array;

a microcontroller;

a characteristics and analysis module;

a machine readable memory; and a control signal generator.

3. The medical implant system of claim 1, wherein the internal pulse generator is in communication with the one or more recording electrodes via one or more cables.

4. The medical implant system of claim 1, wherein the one or more recording electrodes are one of the following: implanted subdurally, implanted epidurally, implanted in the subgaleal space, or an EEG cap.

5. The medical implant system of claim 1, wherein the characteristics and analysis module analyzes recorded field potentials using spectral analysis of at least one of the following frequency bands: delta (<4 Hz), theta (4-8 Hz), alpha (8-12 Hz), beta (12-30 Hz), gamma (30-80 Hz), high-gamma (>80 Hz).

6. The medical implant system of claim 1, wherein the characteristics and analysis module analyzes recorded field potentials for one or more out of the following: peak amplitude, peak-to-trough amplitude, root-mean-square power, and or ratios of any combination of these measures across the one or more recording electrodes.

7. The medical implant system of claim 1, wherein the characteristics and analysis module analyzes recorded field potentials using spectral analysis to determine at least one of the following: the relative mean power as a percentage decrease or increase of mean power relative to a baseline for any spectral power band, the ratios of mean power between any two spectral power bands, and the differential power ratios in certain frequency bands across the one or more recording electrodes.

8. The medical implant system of claim 1, wherein the characteristics and analysis module analyzes recorded field potentials across the one or more recording electrodes at different times to determine brain state transitions as they propagate across different brain regions.

9. The medical implant system of claim 1, wherein the characteristics and analysis module analyzes recorded field potentials for vagal evoked potential phases for at least one of the following: peak amplitude, peak-to-trough amplitude, root-mean-square power, or ratios of any combination of these measures across the one or more recording electrodes.

10. The medical implant system of claim 1, wherein the one or more stimulating electrodes are configured to stimulate the vagus nerve to produce vagal evoked potentials.

11. The medical implant system of claim 1, where the characteristics of the recorded field potentials are used to modulate a VNS protocol.

* * * * *